(12) United States Patent
Brodaczewski et al.

(10) Patent No.: US 11,744,595 B2
(45) Date of Patent: Sep. 5, 2023

(54) LIGATING CLIP

(71) Applicant: Grena USA LLC, Wilmington, DE (US)

(72) Inventors: Wieslaw Brodaczewski, Balbriggan (IE); Konrad Brodaczewski, Balbriggan (IE); Andrzej Decewicz, Nottingham (GB); Tomasz Przekopiński, Ząbki (PL)

(73) Assignee: GRENA USA LLC, Wilmington, DE (US)

( * ) Notice: Subject to any disclaimer, the term of this patent is extended or adjusted under 35 U.S.C. 154(b) by 22 days.

(21) Appl. No.: 17/314,308

(22) Filed: May 7, 2021

(65) Prior Publication Data

US 2021/0346028 A1    Nov. 11, 2021

Related U.S. Application Data

(60) Provisional application No. 63/022,650, filed on May 11, 2020.

(51) Int. Cl.
*A61B 17/122* (2006.01)
*A61B 17/12* (2006.01)

(52) U.S. Cl.
CPC .. *A61B 17/122* (2013.01); *A61B 2017/12004* (2013.01)

(58) Field of Classification Search
CPC ................ A61B 17/122; A61B 2017/12004
See application file for complete search history.

(56) References Cited

U.S. PATENT DOCUMENTS

| | | |
|---|---|---|
| 3,867,944 A | 2/1975 | Samuels |
| 4,834,096 A | 5/1989 | Oh et al. |
| 5,062,846 A | 11/1991 | Oh et al. |
| 5,100,416 A | 3/1992 | Oh et al. |
| 6,863,675 B2 | 3/2005 | Wilson, Jr. |
| 6,880,699 B2 | 4/2005 | Gallagher |
| 7,001,412 B2 | 2/2006 | Gallagher et al. |
| 7,211,092 B2 | 5/2007 | Hughett |
| 7,326,223 B2 | 2/2008 | Wilson, Jr. |
| 9,445,820 B2 | 9/2016 | Whiting |
| 10,265,079 B2 | 4/2019 | Brodaczewski |

(Continued)

FOREIGN PATENT DOCUMENTS

| | | |
|---|---|---|
| EP | 0314064 B1 | 12/1994 |
| EP | 00079772 A2 | 1/2009 |

(Continued)

*Primary Examiner* — Shaun L David
*Assistant Examiner* — Rachael L Geiger
(74) *Attorney, Agent, or Firm* — Haug Partners LLP (57) ABSTRACT

A one piece molded polymeric ligating clip comprises a pair of curved jaws having a hinge at a proximal end and a latch at a distal end. The inner face of each jaw includes two rows of transverse ribs, with the rows separated from one another along a longitudinal center line of each jaw. The ribs of one row are staggered with respect to the ribs of the other row of the same jaw as well as ribs of the corresponding rows of the other jaw. Each rib includes a body and a pyramid which projects away from the inner face of its jaw and toward the longitudinal center of its jaw. The pyramid tip comprises a sharp apex which projects across the longitudinal center of its respective jaw.

20 Claims, 12 Drawing Sheets

(56) References Cited

U.S. PATENT DOCUMENTS

| | | |
|---|---|---|
| 2004/0059359 A1 | 3/2004 | Wilson |
| 2005/0165423 A1 | 7/2005 | Gallagher et al. |
| 2006/0217749 A1 | 9/2006 | Wilson |
| 2009/0088783 A1 | 2/2009 | Kennedy |
| 2009/0171380 A1 | 7/2009 | Whiting |
| 2011/0224700 A1 | 9/2011 | Schmidt |
| 2017/0311954 A1* | 11/2017 | Brodaczewski ..... A61B 17/122 |
| 2018/0368852 A1 | 12/2018 | Foshee |

FOREIGN PATENT DOCUMENTS

| | | | |
|---|---|---|---|
| WO | 2013040467 A2 | 3/2013 | |
| WO | WO-2018069690 A1 * | 4/2018 | ........... A61B 17/122 |

* cited by examiner

LIGATING CLIP

RELATED APPLICATIONS

This application claims the benefit of Provisional Application No. 63/022,650 filed 11 May 2020, the entirety of which is incorporated herein by reference.

BACKGROUND OF THE INVENTION

1. Field of the Invention

This invention relates generally to surgical clips and more particularly to polymeric ligating clips.

2. Antecedents of the Invention

Numerous surgical procedures require cutting blood vessels and ducts which might require temporary or permanent ligation. Ligation of vessels or other tissues can be performed by closing the vessel with a ligating clip, or by suturing the vessel with surgical thread. Ligation by suturing required complex and difficult time-consuming manipulations of a needle and suture material. Such complex manipulations were often difficult to perform and diverted attention to the surgical procedure itself. Accordingly, the employment of ligating dips, which are relatively easy and quick to apply has grown dramatically.

Hemostatic and aneurysm clips have been used in surgery for ligating blood vessels or other tissues to stop the flow of blood. Such clips have also been used for interrupting or occluding ducts and vessels in particular surgeries. Ligating clips have been applied to the vessel or other tissue by using a surgical clip applier, ligating clip applier, or hemostatic clip applier.

While metallic ligating dips have been employed, metallic clips have been found to interfere with the imaging techniques such as computer tomography and magnetic resonance imaging. To overcome such limitations, biocompatible polymers have been increasingly used for ligating clips. Unlike metallic clips, which are usually symmetric, polymeric clips are usually asymmetric.

These polymeric ligating clips generally comprise a pair of curved jaws joined at their proximal ends with an integral hinge. The distal end of one jaw terminates in a latch into which the distal end of the other jaw securely fits to lock the jaws together. The distal ends of the jaws of the clips disclosed in U.S. Pat. No. 4,834,096 include lateral bosses that are engaged by jaws of a clip applier which k employed to close the clip around the tissue to be ligated, and to latch or lock the clip in the closed condition. In operation, the jaws of the clip applier are actuated to compress force the bosses toward one another. This causes the jaws to pivot inwardly about the hinge, thereby deflecting the latch of the one jaw to allow reception therein of the distal end of the other jaw.

Ligating dips must have a sufficient degree of damping force and retention on a vessel or duct, so as not to move relative to the vessel or duct when applied, while also preserving tissue integrity and minimizing tissue damage. Among the previous approaches at attaining the appropriate retention were spaced ribs extending transversely across the inner face of each jaw as disclosed in U.S. Pat. No. 5,062,846, a collapsible flexible rib extending longitudinally along the inner face of a jaw, as disclosed in U.S. Pat. No. 9,445,820 and a rib extending longitudinally along the inner face of a jaw which seats in a groove formed in the inner face of the other jaw, as disclosed in Publication No. 2005/0165423 A1.

There remained a need however; to provide a ligating dip capable of being firmly secured to the tissue or vessel walls without slippage with a minimum level of damage to tissue or vessel walls.

SUMMARY OF THE INVENTION

A one piece molded polymeric ligating clip comprises a pair of curved jaws having a unitary hinge at a proximal end and a latch at a distal end. The inner face of each jaw includes two rows of transverse ribs, with the rows separated from one another along a longitudinal center line of each jaw.

The ribs of one row are staggered with respect to the ribs of the other row of the same jaw as well as ribs of the corresponding rows of the other jaw. Each rib includes a pyramid which projects away from the inner face of its jaw and toward the longitudinal center of its jaw. The pyramid tip comprises a sharp apex which projects across the longitudinal center line of its respective jaw. As the jaws are clamped together and close around a vessel or tissue, curved jaws deflect such that the ribs of a row of one jaw shift toward the opposed ribs of the other jaw while the apices the ribs impale the vessel wall or tissue for improved retention and elimination of slippage.

From the foregoing compendium, it will be appreciated that an aspect of the present invention is to provide a polymeric ligating clip of the general character described which is not subject to the aforementioned disadvantages of the antecedents of the invention.

A feature of the present invention is to provide a polymeric ligating clip of the general character described which securely ligates vascular walls with minimal tissue trauma.

A consideration of the present invention is to provide a polymeric ligating clip of the general character described which securely ligates vascular walls while precluding slippage between the vascular walls and the clip.

Another aspect of the present invention is to provide a polymeric ligating clip of the general character described which is well suited for employment with conventional applicators.

A further feature of the present invention is to provide a polymeric ligating clip of the general character described which is well suited for economical mass production fabrication.

An additional consideration of the present invention is to provide a polymeric ligating clip of the general character described which is relatively simple to use.

To provide a polymeric ligating clip of the general character described wherein opposed rows of prongs impale a vascular wall or tissue for improved retention and eliminate slippage is another aspect of the present invention.

An additional feature of the present invention is to provide a one piece unitary polymeric ligating clip of the general character described having a pair of curved jaws with an inner face of each jaw including rows of transverse ribs separated from one another with each rib including a sharp apex projecting away from the inner face of the jaw and across the longitudinal center of the jaw for impaling vascular tissue when the clip is closed.

Other aspects, features and considerations of the present invention in part will be obvious and in part will be pointed out hereinafter.

With these ends in view, the invention finds embodiment in various combinations of elements, arrangements of parts and series of steps by which the above-mentioned aspects, features and considerations and certain other aspects, features and considerations are attained, or with reference to the accompanying drawings and the scope of which will be more particularly pointed out and indicated in the appended claims.

BRIEF DESCRIPTION OF THE DRAWINGS

In the accompanying drawings, wherein one of the various possible exemplary embodiments of the invention is shown.

DESCRIPTION OF THE INVENTION

The present invention will now be described in detail with reference to the drawings, which are provided as illustrative examples of the invention so as to enable those skilled in the art to practice the invention. Notably, the figures and examples below are not meant to limit the scope of the present invention to a single embodiment, but other embodiments are possible by way of interchange of some or all of the described or illustrated elements.

Moreover, where certain elements of the present invention can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein.

Applicants do not intend for any term in the specification or claims to be ascribed an uncommon or special meaning unless explicitly set forth as such. Further, the present invention encompasses present and future known equivalents to the known components referred to herein by way of illustration. As employed herein, the term pyramid shall be construed as a solid geometric form having at least two intersecting planar faces and at least one additional face which is not necessarily planar.

Referring now to the drawings the reference numeral 10 denotes a molded one piece polymeric ligating clip constructed in accordance with the invention. The clip 10 includes a pair of jaws 12, 14. The jaw 12, hereinafter denoted as the upper jaw, includes a distal end 16 and a proximal end 18, The jaw 14, hereinafter denoted as the lower jaw, includes a proximal end 20 and a distal end 22. The proximal ends 18, 20 are joined by an integral unitary hinge 24.

Figure 1:
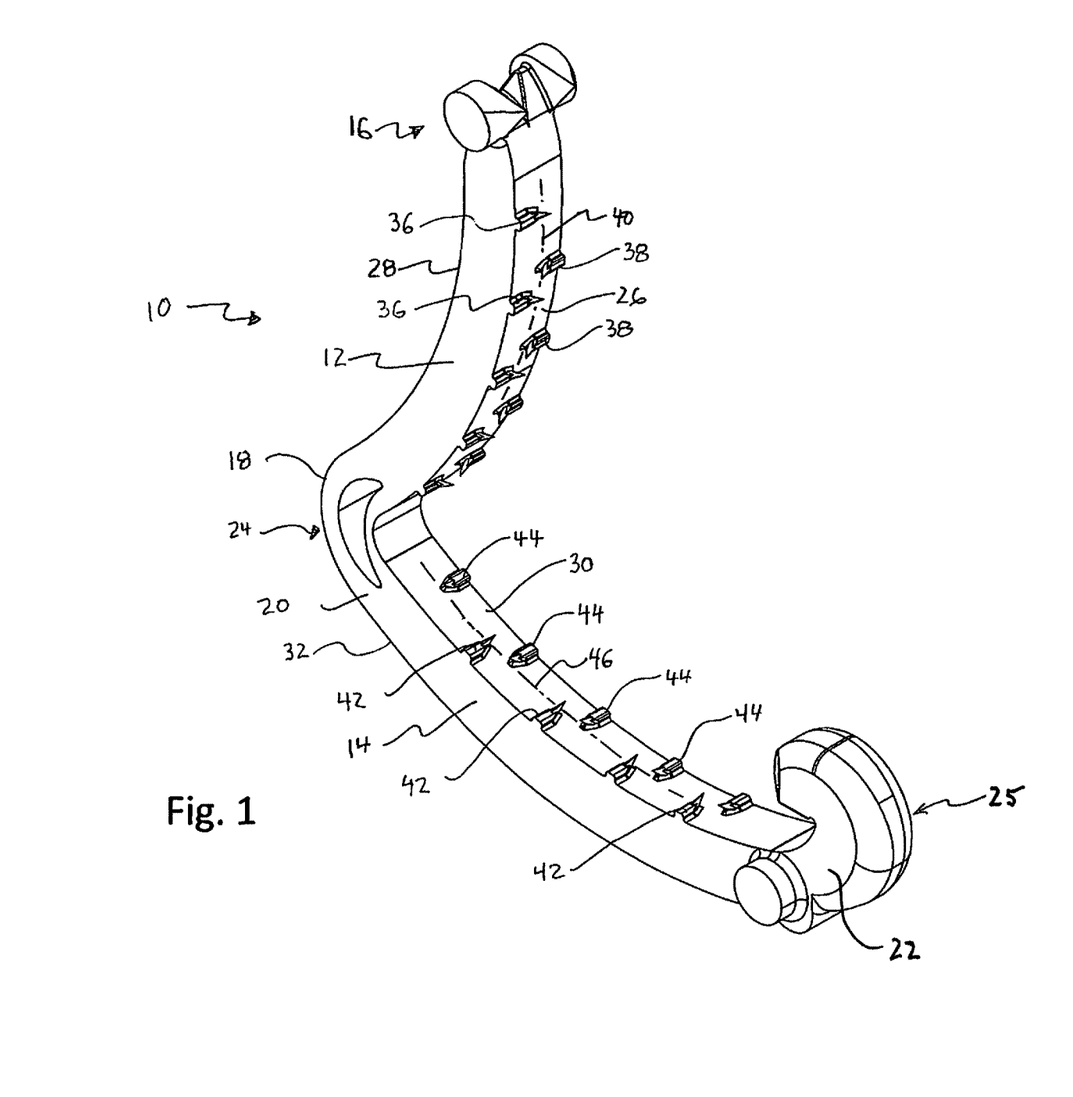
FIG. 1 is an isometric view of a ligating clip constructed in accordance with the invention in an open position and showing a pair of jaws, with each jaw including two rows of ribs having sharp apices for engaging vascular walls.
Figure 2:
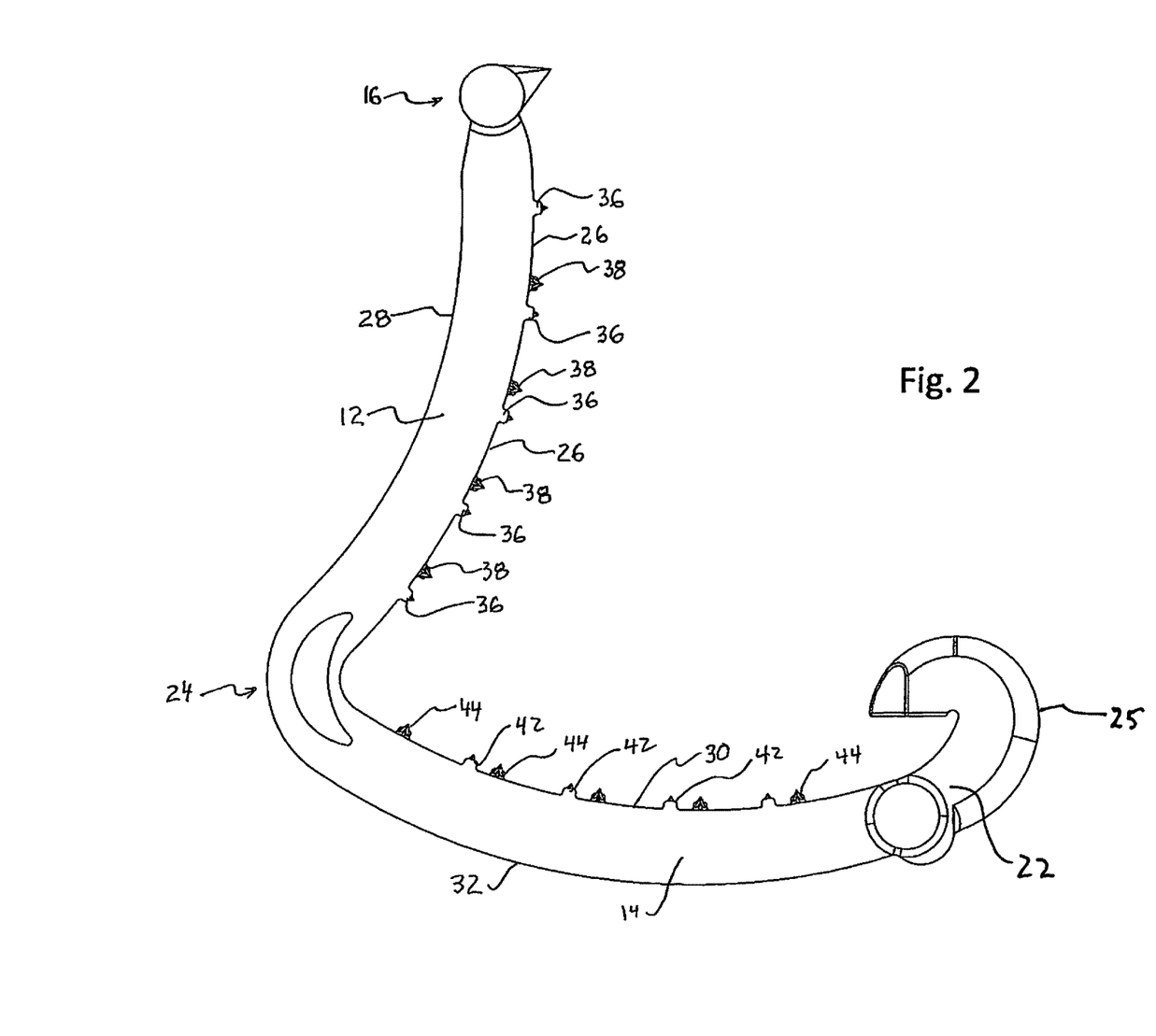
FIG. 2 is a side elevational view of the ligating clip.
Figure 3:
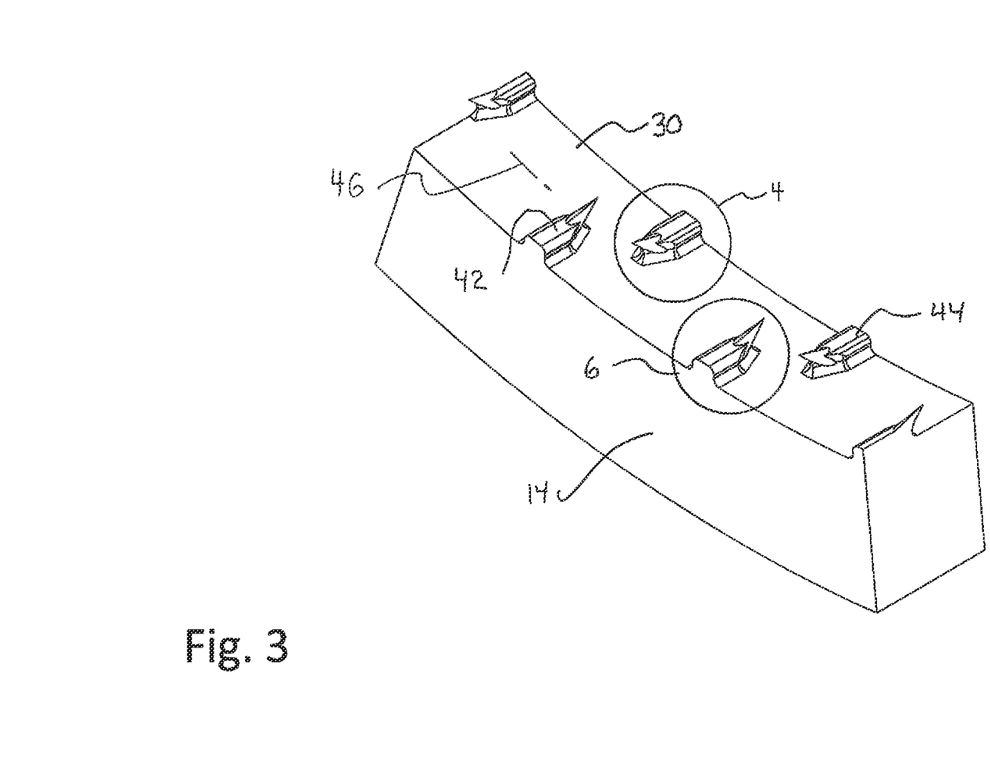
FIG. 3 is an enlarged scale cutaway isometric view of the lower jaw.
Figures 4, 5:
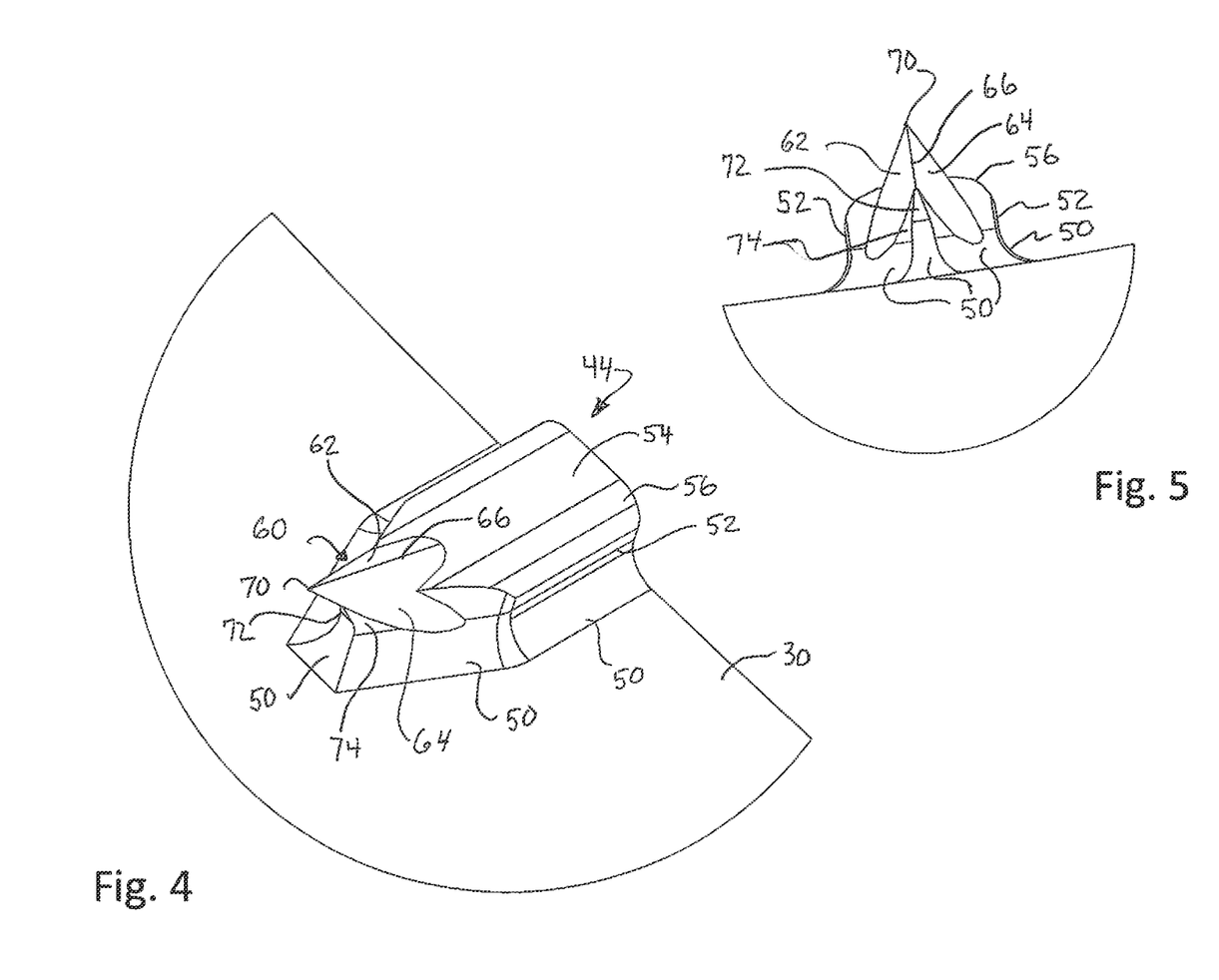
FIG. 4 is an enlarged scale isometric view of a single rib depicted in circle 4 of FIG. 3.
FIG. 5 is a front elevational view of the rib depicted in FIG. 4.
Figure 6:
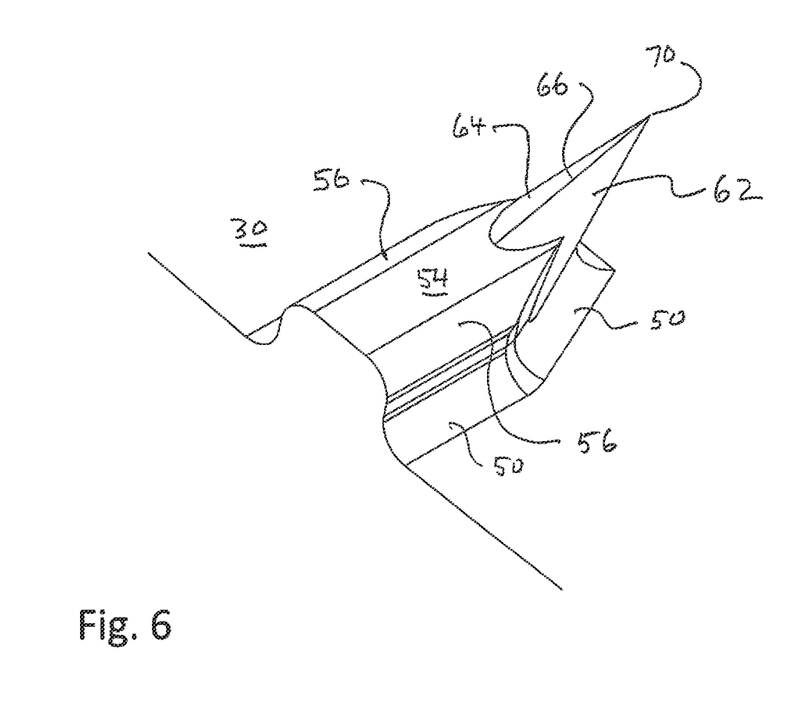
FIG. 6 is an enlarged scale isometric view of a single rib depicted in circle 6 of FIG. 3.
Figure 7:
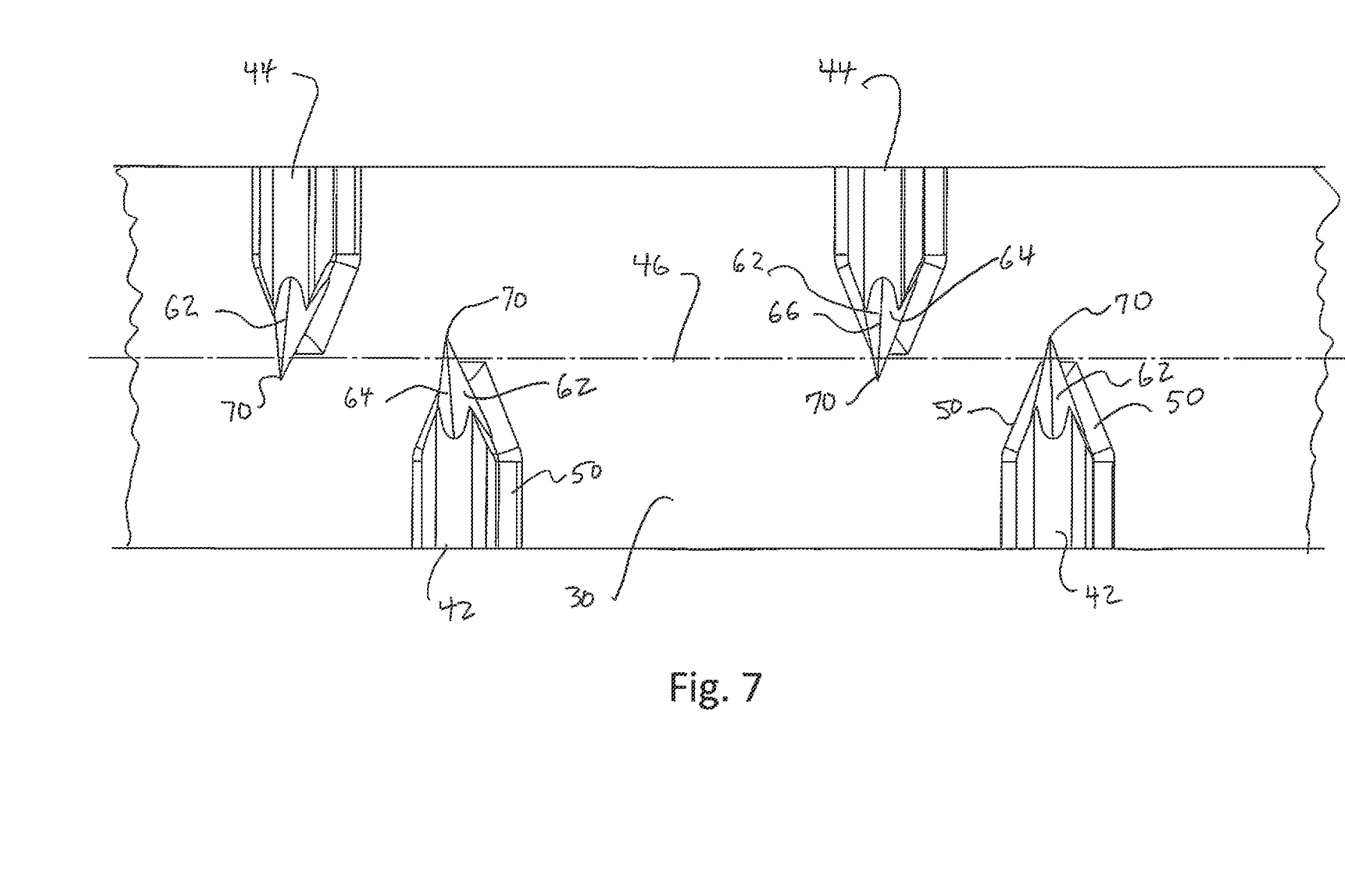
FIG. 7 is an enlarged scale fragmentary plan view of the inner face of the lower jaw showing pyramid tips of the ribs extending across a longitudinal center line of the jaw.
Figure 8:
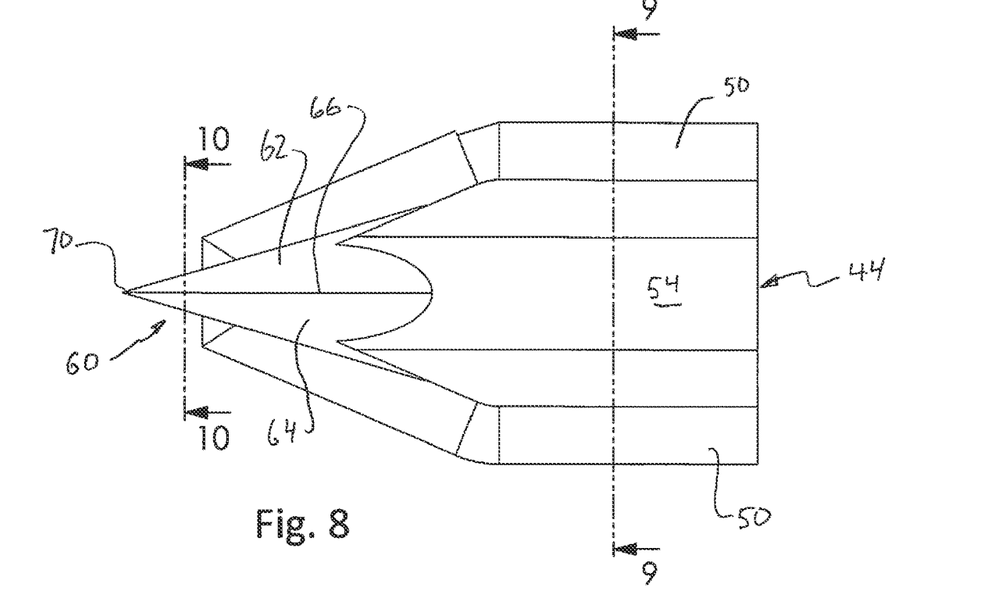
FIG. 8 is an enlarged scale plan view to the rib depicted in FIG. 4.
Figure 9:
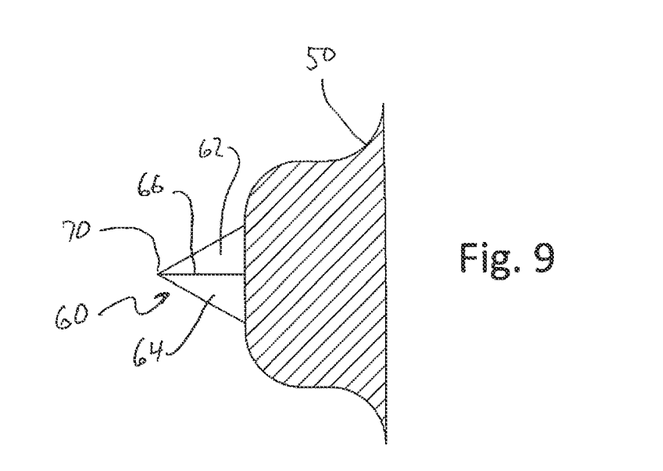
FIG. 9 is a sectional view through the rib, the same being taken along the plane 9-9 of FIG. 8.
Figure 10:
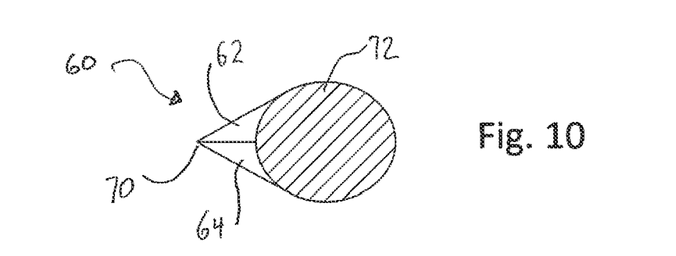
FIG. 10 is a sectional view through a pyramid tip of the rib, the same being taken along the plane 10-10 of FIG. 8.
Figure 11:
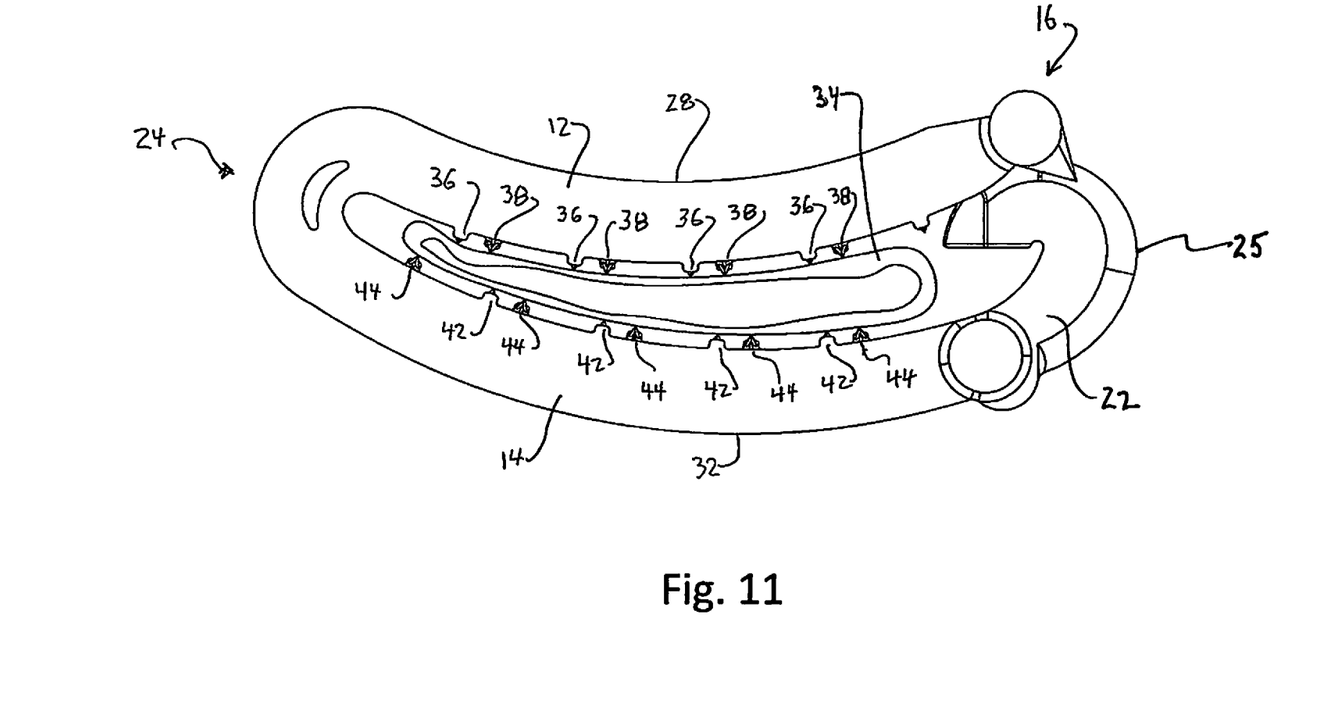
FIG. 11 is a side elevation view of the ligating clip taken as the clip is beginning to clamp a vessel.
Figure 12:
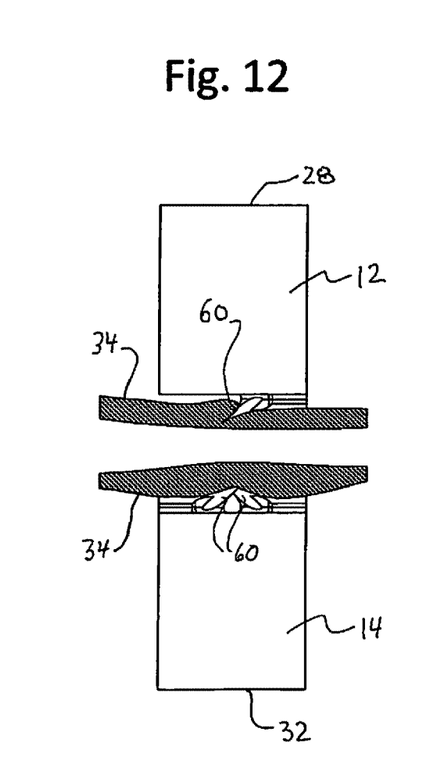
FIG. 12 is an enlarged scale transverse sectional view through the clip and vessel of FIG. 11, and showing initial engagement between the ribs pyramids and the vessel taken along broken planes.
Figure 13:
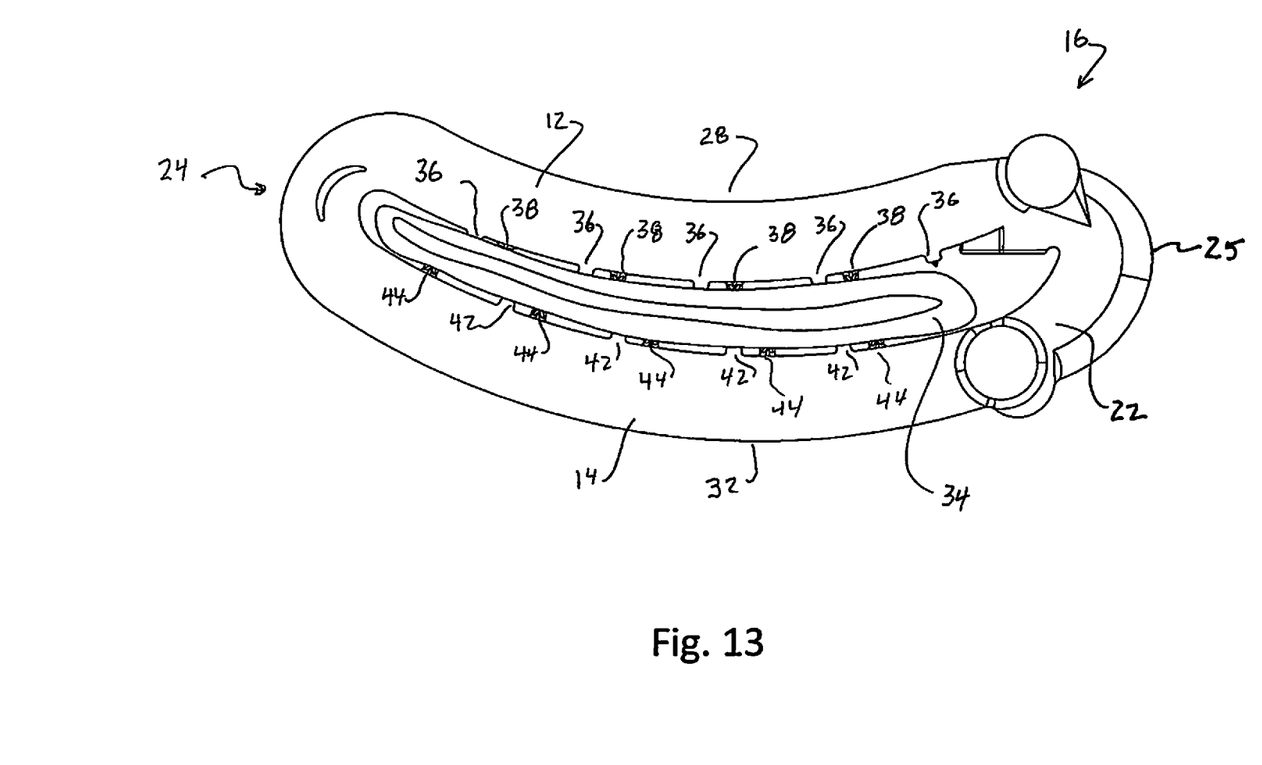
FIG. 13 is a side elevation view of the ligating clip taken as the clip continues to clamp the vessel, but prior to latching the jaws.
Figure 14:
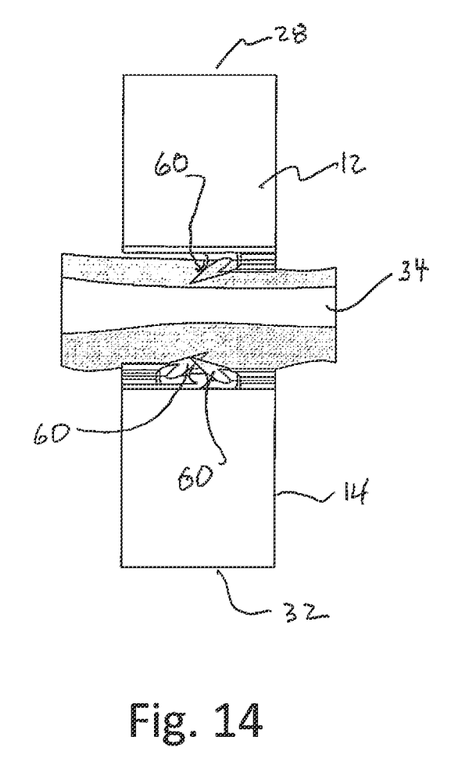
FIG. 14 is an enlarged scale transverse sectional view through the clip and vessel of FIG. 13, taken along broken planes.
Figure 15:
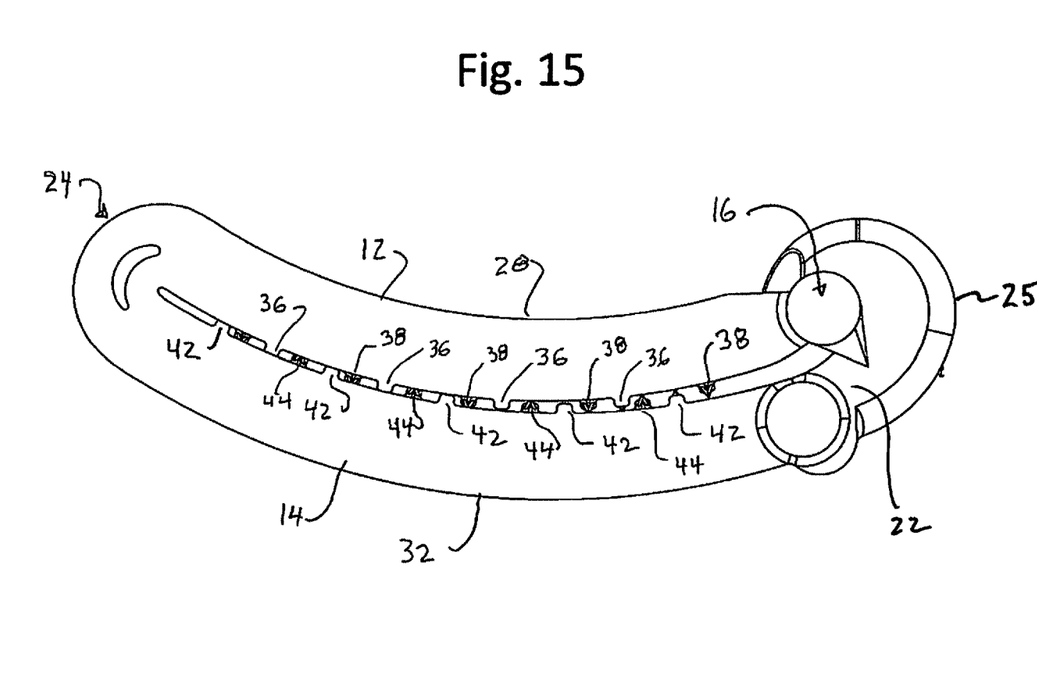
FIG. 15 is a side elevation view of the ligating clip, with the clamp closed and latched.
Figure 16:
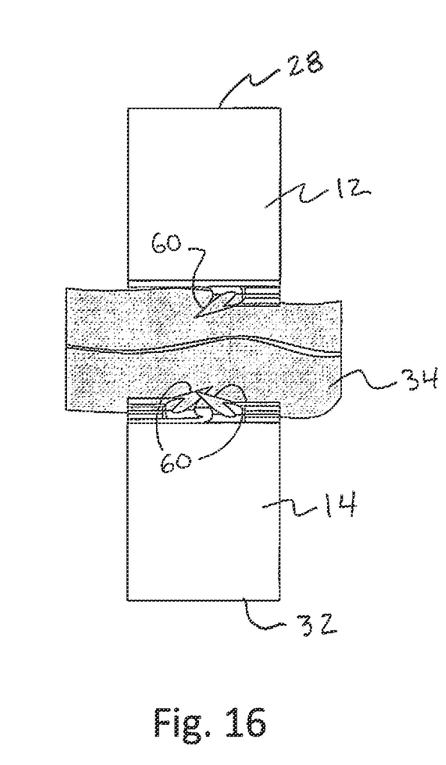
FIG. 16 is an enlarged scale transverse sectional view through the clip and vessel of FIG. 15 taken along broken planes, showing the vessel fully closed with the jaws and prongs impaled into to the vessel wall.
Figure 17:
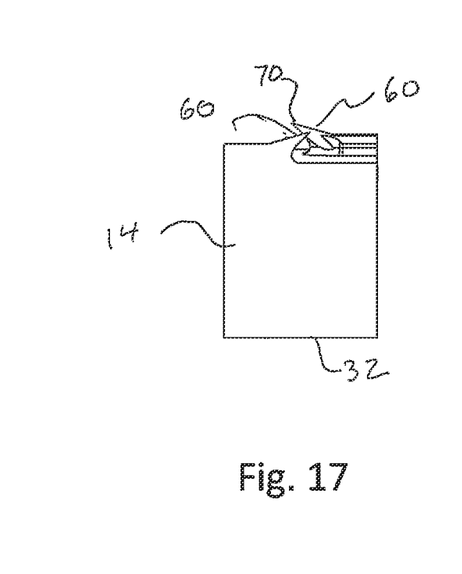
FIG. 17 is an enlarged scale sectional view through the lower jaw as viewed from the right in FIG. 3.

As shown in FIGS. 1 and 2, the upper jaw 12 has a convex inner vessel damping face 26 and a concave outer face 28, while the lower jaw 14 has a concave inner vessel clamping face 30 and a convex outer face 32.

A latch 25 for joining the distal ends 16, 22, is fully described in U.S. Pat. No. 10,265,079 which is incorporated herein in its entirety by reference. The latch 25 is integral with the distal end 22.

In the practice of ligating a vessel as understood by persons skilled in the art, the clip 10 is designed to be compressed into a latched or locked position around a vessel or duct 34 through the use of an appropriate dip applicator instrument, such as described in U.S. Pat. Nos. 5,100,416, 5,062,846 or 6,863,675, all of which are incorporated herein by reference. The clip applicator instrument is actuated to cause the jaws 12, 14 to close around the vessel 34 as described in U.S. Pat. No. 10,265,079

Pursuant to the invention, the inner face 26 of the upper jaw 12 includes two rows of transverse ribs 36, 38, with the rows separated from one another along a longitudinal center line 40. The ribs 36 of one row are staggered with respect to the ribs 38 of the other row. Similarly the inner face 30 of the lower jaw 14 includes two rows of transverse ribs 42, 44, with the rows separated from one another along a longitudinal center line 46. The ribs 42 of one row are staggered with respect to the ribs 44 of the other row as well as the ribs 36, 38 of the jaw 12.

Pursuant to the invention, each rib 36, 38, 42, and 44 includes an elongate body which projects away from its respective jaw clamping face 26, 30 and extends laterally from a peripheral edge if its respective jaw toward the longitudinal centerline of its respective jaw. With reference to FIGS. 4-6 and 9, it will be noted that the rib body is unitary with the jaw, and extends away from the clamping faces at a fillet 50. Projecting from the fillet 50, the body includes planar wall segments 52 which are perpendicular to the inner faces of the respective jaws. The rib body includes a planar top surface 54. A curved surface 56 joins the wall segments to the top surface.

Each rib includes a pyramid 60, which projects away from and beyond the rib body, toward the longitudinal center of its jaw and away from the inner face of its respective jaw. The pyramid 60 comprises two planar panels 62, 64 which intersect along a line 66. By way of example, the panels 62, 64 intersect at an angle of 60°. The tip or distal end of the pyramid 60 comprises a sharp apex 70 which projects across and beyond the longitudinal center line of its respective jaw. Reinforcing support for the apex 70 is provided by a flange 72 which extends from the fillet 50 to the apex 70. A curved transition wall 74 extends from the fillet 50 to the underside of the pyramid 60.

As the upper jaw 12 and the lower jaw 14 close around the vessel or duct 34, the ribs 36, 38, 42 and 44 force portions of the vessel wall or tissue into the spaces between the ribs while the apices and pyramids impale the vessel wall or tissue an prevent movement of the clip 10 or vessel 34 relative to one another. As the jaws close, the apices of the ribs 36 are shifted toward the apices of the ribs 44 and the apices of the ribs 42 are shifted toward the apices of the ribs 38.

To ligate a vessel or duct in accordance with the invention the following steps are employed: a) providing the ligating clip in the open position, b) grasping the ligating clip at or adjacent the distal end of each jaw; c) positioning the inner faces of the jaws across the vessel or duct to be ligated; d) impaling the sharp apices of the pyramids into the wall of the vessel or duct by applying compressive force urging the distal ends together; and e) terminating step d) when the latch is engaged.

Polymeric ligating clips of standard sizes are commonly used in number of surgical procedures. The thicker the tissue or the higher blood pressure in the vessel, the more difficult is to close it with a clip and the clip is more likely to dislodge. Dislodgement from a large vessel, or structure, e.g., a lung or appendix, is a life threatening situation. The polymeric ligation clips in accordance with U.S. Pat. No. 10,265,079 are much more stable on the tissue and more resistant to dislodgement, because apart from clamping, the clips anchor in the tissue.

The largest currently available ligation clip is still too small for some tissues. Usage of ligation clip sized in accordance with the present invention will permit employment in a broader spectrum of surgical applications and will result in a quick, easy, low cost and reliable procedure for ligation. The clip of the present invention was designed for challenging applications and thick tissues. The jaws are longer and thicker than the jaws of prior clips.

The rib configuration of the present invention allows for firmer anchoring of ribs in the tissue, preventing the clip from dislodgement more effectively than clips of the prior art. By way of example, It has been found that clips of the present invention having a length of approximately 24 mm plus or minus 20% from the hinge 24 to the latch 25 would be well suited for implementation in the following procedures due to enhanced stability and dimensional configuration:

1. Laparoscopic appendectomy—standard surgical procedure used in the treatment of appendicitis. Can be carried out as laparoscopic or open surgery. One of the important steps of the procedure requires appendiceal stump closure. Few surgical techniques are used for this step—sutures, endoloops, staplers or XL clips. Sutures are reliable, relatively low in cost and placement can be relatively quick, but in open surgery only, where the appendix is well exposed. As laparoscopic surgery becomes more popular, sutures, although technically possible, are not comfortable for the surgeon and are time consuming, so rather not used for laparoscopic appendectomies.

A comfortable, easy, fast and reliable solution for laparoscopic appendectomy came with endostaplers. They deploy two triplicated rows of staples and cut tissue between them. But a disadvantage of endostaplers is that its disposal puts a heavy burden on the environment. Another disadvantage of endostaplers is their cost; employment of endostaplers is the most expensive technique used for appeniceal stump closure.

To reduce costs and overcome discomfort, endoloops were designed wherein sutures are combined with a laparoscopic delivery device. While low in cost, this procedure requires a more thorough preparation of the appendix and its mesoappendix and utilizing an endoloop is more difficult than a stapler. Low cost of device can be overcome by increased duration of operation.

Due to the high price of staplers and questionable cost reduction with endoloops, polymer clips are recently commonly used in laparoscopic appendectomy. They are comparable to sutures in terms of cost, fast, easy to use and have the same reliability as sutures or staples. A disadvantage of currently available polymer clips is their size which is too small to close bigger appendixes which are quite common. In such cases surgeon must use staples or endoloops.

The polymer clip of the present invention offers surgeons an implement suitable for any size appendix which has the same reliability as the heretofore mentioned closure techniques. It is fast and convenient as endostaples, and low in cost like sutures; it combines the advantages of currently used methods without their disadvantages.

2. Thoracoscopic resection of small peripheral lung tumors or lung biopsy—thoracoscopic surgery has become more and more popular as compared to open procedures, recovery time is shorter and comfort of life much better with similar long term results. As thoracoscopic procedures are, in general, similar to laparoscopic ones, sutures are not recommended as are time consuming and uncomfortable. For above reason endostaplers, endoloops or polymer clips are used.

Endostaplers, require a minimum of 4.5 cm of intrathoracic space to open, making its use in patients less than 10 kg impractical. Required space is not a limit for adult patients, but it is the most expensive technique currently used. There are numerous reports in the literature about complications after staple application in lung surgery. The staple line is not always tight, as lungs regularly expand and collapse while breathing. For this reason reinforcement material or additional sealing of the staple line may be necessary which increases the high procedure cost.

Endoloops are a relatively inexpensive and easy to use solution for thoracoscopic resections and biopsies and are commonly used. Delivery devices for the loop are rigid and straight, which might limit possibility to use this technique in some cases with restricted access.

Polymeric ligation clips in accordance with U.S. Pat. No. 10,265,079 are much more reliable for secure tissue closure due to an anchoring feature. Angled clip appliers such as those described in US2019133596 facilitate access to the most restricted areas which are not accessible by endoloops or endostaplers. But even the largest currently available clip is too small for many tumors, which limits wider use of this cheap, convenient, easy and reliable technique. The polymer clip of the present invention will contribute to safer lung surgery and diagnostics.

3. Nephrectomy—to perform nephrectomy, large renal vessels must be permanently closed. There is high pulsatile blood pressure in the renal artery, what is a challenge for any ligating device. Of special concern are live donor nephrectomies as kidney donor is a healthy, usually relatively young person. Only two ligating techniques are currently used for these applications—staplers and polymer clips. Staplers, including endostaplers, are popular but extremely expensive. There are also many reports of complications including haemorrhage after staple application on high pressure vessels. There are also medical articles indicating that staples are not as reliable as polymer clips in case of high pulsatile blood pressure and their stability greatly differs between devices, even from the same manufacturer.

Polymer clips are safe, reliable and commonly used, but due to adverse consequences in the US after laparoscopic live donor nephrectomy, polymer clips of all the manufacturers have been contraindicated for this procedure. It is likely that those complications were due to user mistake, not clip itself, but the polymer clips of the present invention, due to their improved rib configuration are expected to be stable enough to cancel contraindication for live donor nephrectomy.

4. Pneumonectomy—The pulmonary artery and vein must be ligated during total lung resection. They are large vessels, especially the pulmonary artery, the diameter of which is usually between 15 and 20 mm. Due to the size of these vessels, staplers, including endostaplers, are recently the only ligation implements currently utilized for pulmonary vessels closure and transection. As for other procedures stapling is expensive technique but cannot be widely replaced.

Polymer clips currently accessible on the market cannot be used as the largest available size was designed to close vessels up to 16 mm, so pulmonary vessels are usually out of theoretical possibilities for polymer clips. Polymer clips of the present invention are expected to be able to safely close such large vessels such as pulmonary arteries and veins for a fraction of the cost of utilizing a stapler.

The particular combinations of elements and features in the above-detailed embodiment are exemplary only; the interchanging and substitution of these teachings with other teachings in this application are also expressly contemplated. As those skilled in the art will recognize, variations, modifications, and other implementations of what is described herein can occur to those of ordinary skill in the art without departing from the spirit and the scope of the invention as claimed.

Further, in describing the invention and in illustrating embodiments of the invention in the figures, specific terminology, numbers, dimensions, materials, etc, are used for the sake of clarity. However the invention is not limited to the specific terms, numbers, dimensions, materials, etc, so selected, and each specific term, number, dimension, material, etc., at least includes all technical and functional equivalents that operate in a similar manner to accomplish a similar purpose. Use of a given word, phrase, number, dimension, material, language terminology, product brand, etc. is intended to include all grammatical, literal, scientific, technical, and functional equivalents. The terminology used herein is for the purpose of description and not limitation.

Having described the preferred embodiment of the invention, it will now become apparent to one of ordinary skill in the art that other embodiments incorporating the concept may be used. Moreover, those of ordinary skill in the art will appreciate that the embodiment of the invention described herein can be modified to accommodate and/or comply with changes and improvements in the applicable technology and standards referred to herein.

Variations, modifications, and other implementations of what is described herein can occur to those of ordinary skill in the art without departing from the spirit and the scope of the invention as claimed. It is felt therefore that these embodiments should not be limited to the disclosed embodiment but rather should be limited only by the spirit and scope of the appended claims.

Having thus described the invention there is claimed as new and desired to be secured to Letters Patent:

1. A ligating clip comprising a first jaw and a second jaw, each jaw having a proximal end and a distal end, the jaws being joined at their proximal ends by a hinge, each jaw having an inner face and an outer face, the jaws being pivotable about the hinge from an open operating position, wherein the inner faces of the jaws are positioned about a vessel or duct of a patient, to a closed operating position, wherein the distal ends are joined by a latch and the vessel or duct is compressed between the inner faces of both jaws, a first row of evenly spaced ribs projecting from the inner face of the first jaw and a second row of evenly spaced ribs projecting from the inner face of the first jaw, the rows being spaced from one another about a longitudinally extending center line along the inner face of the first jaw, the ribs of the first row being staggered with respect to the ribs of the second row, the ligating clip comprising at least one rib of the first row comprising
    a body extending from the inner face of the first jaw at a fillet and planar wall segments projecting from the fillet that are perpendicular to the inner face of the first jaw, the body facing the longitudinally extending center line of the inner face of the first jaw and comprises a planar top surface, and a pyramid having a sharp tip projecting beyond the body and away from the inner face of the first jaw, the pyramid of the first row extending across the longitudinally extending center line of the inner face of the first jaw, and
    at least one rib of the second row comprising
    a body extending from the inner face of the first jaw at a fillet and planar wall segments projecting from the fillet that are perpendicular to the inner face of the first jaw, the body of the at least one rib of the second row comprises a planar top surface, and a pyramid having a sharp tip projecting beyond the body of the at least one rib of the second row and away from the inner face of the first jaw, the pyramid of the second row projecting toward the longitudinally extending center line of the inner face of the first jaw, whereby the sharp tips of the pyramids of the at least one rib of the first row and the at least one rib of the second row are configured to impale a wall of a vessel or duct and prevent movement of the clip relative to the vessel or duct when the clip is in the closed position while minimizing tissue trauma.

2. The ligating clip of claim 1, the improvement further comprising:
    a third row of evenly spaced ribs, the ribs of said third row projecting from the inner face of the second jaw and
    a fourth row of evenly spaced ribs, the ribs of said fourth row projecting from the inner face of the second jaw, the ribs of the third and fourth rows being spaced from one another a long the longitudinally extending center line of the inner face of the second jaw, the ribs of the third row being staggered with respect to the ribs of the fourth row and with respect to the ribs of the first and second rows, at least one rib of the third row having a body extending from the inner face of the second jaw at a fillet and planar wall segments projecting from the fillet that are perpendicular to the inner face of the second jaw, the body having one end facing the longitudinally extending center line of the inner face of the second jaw, and comprises a planar top surface, and a pyramid having a sharp tip projecting beyond the one end of the body of the least one rib of the third row and away from the inner face of the second jaw, the pyramid projecting toward the longitudinally extending center line of the inner face of the second jaw, at least one rib of the fourth row having a body extending from the inner face of the second jaw at a fillet and planar wall segments projecting from the fillet that are perpendicular to the inner face of the second jaw, the body having one end facing the longitudinally extending center line of the inner face of the second jaw, and comprises a planar top surface, and a pyramid having a sharp tip projecting beyond the one end of the body of the at least one rib of the fourth row and away from the inner face of the second jaw and projecting toward the longitudinally extending center line of inner face of the second jaw, whereby the sharp tips of the pyramids of both jaws may impale a wall of the vessel or duct and prevent movement of the clip relative to the vessel or duct when the clip is in the closed operating position.

3. The ligating clip of claim 2, wherein all of the ribs include a body and a pyramid having a sharp tip projecting toward the longitudinally extending center line of the inner face of its respective jaw.

4. The ligating clip of claim 3, wherein the pyramids comprise a tapered projection extending beyond the one end of each body, the sharp tip being at the end of the tapered projection.

5. The ligating clip of claim 1, wherein the pyramids comprise a tapered projections projection and the sharp tips comprise apices.

6. The ligating clip of claim 5, wherein the pyramids comprise a solid geometric form having at least two intersecting planar faces and at least one additional face which is not necessarily planar.

7. A clip for ligating a vessel or duct of a patient, the clip comprising:

first and second jaws having respective proximal and distal end portions, the proximal end portions being joined by a hinge, the first and second jaws having respective first and second inner faces adapted for positioning about a vessel or duct and which may engage the vessel or duct when said first and second jaws are moved about said hinge from an open position to a closed position, wherein the distal end portions are secured together by a latch, said first jaw comprising a first row of evenly spaced ribs, each rib of the first row having a body extending from an inner surface of the first jaw at a fillet and planar wall segments projecting from the fillet that are perpendicular to the inner face of the first jaw, and comprises a planar top surface, and a tapered pyramid extending beyond each body toward a longitudinally extending center line of the inner face of the first jaw, the tapered pyramid of the first row having a sharp tip at its distal end and a second row of evenly spaced ribs, a second row of evenly spaced ribs, each rib of the second row having a body extending from an inner surface of the first jaw at a fillet and planar wall segments projecting from the fillet that are perpendicular to the inner face of the first jaw, and comprises a planar top surface, and a tapered pyramid extending beyond each body toward the longitudinally extending center line of the inner face of the first jaw, the tapered pyramid of the second row having a sharp tip at its distal end, the sharp tips extending across the longitudinally extending center line of the inner face of the first jaw, whereby the tapered pyramids in a closed position is configured to impale a wall of the vessel or duct and prevent movement of the clip relative to the vessel or duct when the clip is in the closed position.

8. The clip of claim 7, wherein the ribs are staggered with respect to one another.

9. The clip of claim 7 wherein, the second jaw comprises a third row of evenly spaced ribs, each rib of the third row having a body extending from an inner surface of the second jaw at a fillet and planar wall segments projecting from the fillet that are perpendicular to the inner face of the second jaw, and comprises a planar top surface, and a tapered pyramid extending beyond each body toward and across a longitudinally extending center line of the inner face of the second jaw, the tapered pyramid of the third row having a sharp apex at its distal end, and a fourth row of evenly spaced ribs, each rib of the fourth row having a body extending from an inner surface of the second jaw at a fillet and planar wall segments projecting from the fillet that are perpendicular to the inner face of the second jaw, and comprises a planar top surface, and a tapered pyramid extending beyond each body toward and across the longitudinally extending center line of the inner face of the second jaw, the tapered pyramid of the fourth row having a sharp apex at its distal end whereby the pyramids of both jaws may impale the wall of the vessel or duct and prevent movement of the clip relative to the vessel or duct when the clip is in the closed position.

10. The clip of claim 1, wherein the clip has a length configured to be in medical procedures selected from the group consisting of laparascopic appendectomy, thorascopic lung biopsy or resection, nephrectomy and pneumonectomy.

11. The clip of with claim 10, wherein the clip has a length of approximately 24 mm from the hinge to the latch.

12. A method of ligating the vessel or duct with the clip of claim 9, the method comprising the steps of:
a) grasping the clip by the distal end portions;
b) positioning the inner faces of the jaws across the vessel or duct to be ligated;
c) impaling the sharp apices and portions of the pyramids into the wall of the vessel or duct by applying compressive force urging the distal end portions together; and
d) terminating step c) when the latch is engaged.

13. A ligating clip comprising a first jaw and a second jaw, each jaw having a proximal end and a distal end, the jaws being joined at their proximal ends by a hinge, each jaw having an inner face and an outer face, the jaws being pivotable about the hinge from an open operating position, wherein the inner faces of the jaws are positioned about a vessel or duct of a patient, to a closed operating position, wherein the distal ends are joined by a latch and the vessel or duct is compressed between the inner faces of both jaws, the ligating clip comprising:

first and second rows of evenly spaced ribs, the rows being spaced from one another along a longitudinally extending center line of the inner face of the first jaw, each rib comprising a body extending away from the inner face of the first jaw at a fillet, and planar wall segments projecting from the fillet that are perpendicular to the face of the first jaw, the body having a planar top surface and a pyramid, the pyramids projecting outwardly from the inner face of the first jaw, the pyramids being inclined toward and beyond the longitudinally extending center line of the inner face of the first jaw, whereby the pyramids may impale a wall of the vessel or duct and prevent relative movement between the clip and the vessel or duct while minimizing tissue trauma when the clip is in the closed operating position.

14. The ligating clip of claim 13, the ligating clip further comprising:

third and fourth rows of evenly spaced ribs on the inner face of the second jaw, each rib comprising a body having a planar top surface and a pyramid, the third and fourth rows being spaced from one another along a longitudinally extending center line of the inner face of the second jaw, the ribs of the third row being staggered with respect to the ribs of the fourth row and with respect to the ribs of the first jaw, each rib of the third and fourth rows including a pyramid projecting outwardly from the inner face of the second jaw, the pyramids being inclined toward the longitudinally extending center line of the inner face of the first jaw, whereby the pyramids of both jaws are configured to impale the wall of the vessel or duct and prevent relative movement between the clip and the vessel or duct when the clip is in the closed operating position.

15. The ligating clip of 7, wherein the ligating clip is polymeric and formed of one piece molded construction.

16. The ligating clip of claim 1, wherein the inner face of the first jaw is concavely curved and the inner face of the second jaw is convexly curved.

17. A method of ligating the vessel or duct with the ligating clip of claim 13, the method comprising:
 a) providing the improved ligating clip in the open operating position,
 b) grasping the improved ligating clip at or adjacent the distal end of each jaw;
 c) positioning the inner faces of the jaws across the vessel or duct to be ligated;
 d) impaling the sharp apices of the pyramids into the wall of the vessel or duct by applying compressive force urging the distal ends together; and
 e) terminating step d) when the latch is engaged.

18. The clip of claim 9, wherein the ribs of the third row are staggered with respect to the ribs of the fourth row and with respect to the ribs of the first jaw.

19. The clip of claim 9, wherein the clip has a length configured to be used in medical procedures selected from the group consisting of laparoscopic appendectomy, thorascopic lung biopsy or resection, nephrectomy and pneumonectomy.

20. The clip of claim 19, wherein the clip has a length of approximately 24 mm from the hinge to the latch.

* * * * *